United States Patent
Reusch et al.

(10) Patent No.: US 9,023,104 B2
(45) Date of Patent: May 5, 2015

(54) BREAST PROSTHESIS

(75) Inventors: Michaela Reusch, Freilassung (DE);
Isabella Baum, Munich (DE); Helmut Wild, Stephanskirchen (DE)

(73) Assignee: Amoena Medizin-Orthopadie-Technik GmbH (DE)

( * ) Notice: Subject to any disclaimer, the term of this patent is extended or adjusted under 35 U.S.C. 154(b) by 550 days.

(21) Appl. No.: 13/180,078

(22) Filed: Jul. 11, 2011

(65) Prior Publication Data

US 2012/0259412 A1    Oct. 11, 2012

(30) Foreign Application Priority Data

Apr. 11, 2011   (DE) .................... 20 2011 005 141 U

(51) Int. Cl.
*A61F 2/52*   (2006.01)
*A61F 2/12*   (2006.01)

(52) U.S. Cl.
CPC ........... *A61F 2/52* (2013.01); *A61F 2250/0024* (2013.01); *A61F 2250/0063* (2013.01); *A61F 2250/0015* (2013.01); *A61F 2250/0062* (2013.01); *A61F 2/12* (2013.01); *A61F 2250/0009* (2013.01); *A61F 2002/523* (2013.01); *A61F 2250/001* (2013.01)

(58) Field of Classification Search
CPC ........ A61F 2/52; A61F 2/12; A61F 2002/523
USPC ................. 623/7–8; 450/54–55, 57
See application file for complete search history.

(56) References Cited

U.S. PATENT DOCUMENTS

| | | | | |
|---|---|---|---|---|
| 3,568,681 | A | * | 3/1971 | Comollo ........................ 450/54 |
| 4,681,587 | A | * | 7/1987 | Eberl et al. ....................... 623/7 |
| 4,795,464 | A | | 1/1989 | Eberl et al. |
| 5,098,330 | A | * | 3/1992 | Greenberg ...................... 450/55 |
| 5,603,791 | A | * | 2/1997 | Weber-Unger et al. ........ 156/145 |
| 5,607,473 | A | | 3/1997 | Weber-Unger et al. |
| 6,113,634 | A | * | 9/2000 | Weber-Unger et al. .......... 623/7 |
| 6,451,139 | B1 | * | 9/2002 | Weber-Unger et al. ......... 156/61 |
| 6,679,912 | B2 | | 1/2004 | Stelter |
| 2006/0025859 | A1 | | 2/2006 | Stelter et al. |
| 2007/0055371 | A1 | * | 3/2007 | Laghi ............................... 623/7 |

FOREIGN PATENT DOCUMENTS

| | | |
|---|---|---|
| DE | 83 11 438 U1 | 4/1983 |
| DE | 87 01 925 U1 | 7/1987 |
| DE | 93 15 935 U1 | 2/1995 |
| DE | 44 21 516 C1 | 7/1995 |
| DE | 20 2004 011 988 U1 | 1/2006 |

(Continued)

OTHER PUBLICATIONS

German Search Report dated May 30, 2012; 5 pages.

(Continued)

*Primary Examiner* — Andrew Iwamaye
(74) *Attorney, Agent, or Firm* — Carter, DeLuca, Farrell & Schmidt, LLP

(57) ABSTRACT

A breast prosthesis is provided having a support shell which is accommodated in a fabric cover, wherein one or more filling chambers for accommodating a filler material is/are located at the rear side of the breast prosthesis, wherein the breast prosthesis has a silicone shell which is arranged in front of the support shell and which is accommodated in the fabric cover in removable manner.

21 Claims, 1 Drawing Sheet

(56) References Cited

FOREIGN PATENT DOCUMENTS

| | | | |
|---|---|---|---|
| DE | 10 2008 050 362 A1 | 4/2010 | |
| DE | 102008050362 A1 * | 4/2010 | ............... A61F 2/52 |
| EP | 0 125 400 A1 | 11/1984 | |
| EP | 0 808 615 A2 | 11/1997 | |
| EP | 1 232 733 A1 | 8/2002 | |

OTHER PUBLICATIONS

European Search Report correpsonding to European Application No. EP 12 00 2422, completed on Jul. 12, 2012 and mailed on Jul. 23, 2012; 3 pages.

* cited by examiner

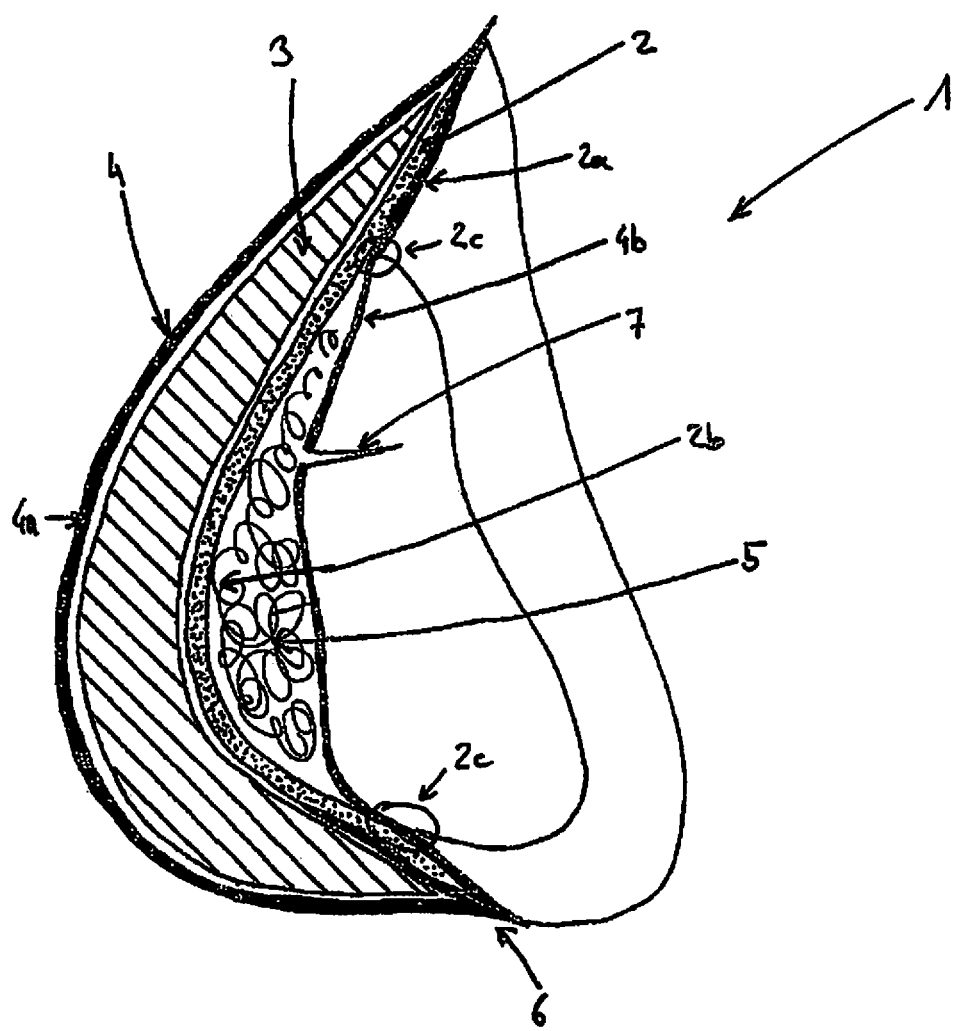

BREAST PROSTHESIS

This application claims priority to German Application No. 20 2011 005 141.2, filed Apr. 11, 2011, the entire contents of which are hereby incorporated by reference.

The invention relates to a breast prosthesis for the replacement of a female breast at least partly surgically removed.

Generic breast prostheses are known from the prior art.

A new technique in the surgical removal and subsequent reconstruction of damaged breast tissue has become established over the last few years. It is thus possible to remove the complete breast tissue, where possible via the areola, so that the "breast shell" is maintained. An expander is then inserted beneath the pectoral muscle to prepare for a later implant supply. The pectoral muscle, however, needs a certain time to expand. The expander is therefore typically initially inserted with a small volume and this volume is only increased successively over a period of weeks or months until the volume of the implant to be inserted has been reached. After a certain holding period, the expander is subsequently replaced with a permanent implant.

A breast prosthesis which is worn as an accompaniment to the aforesaid technique during the regeneration phase and expansion phase thus has to be adapted to a successively changing size of the remaining breast.

It is known from the prior art for this purpose to use a prosthesis for first care instead of a known silicone prosthesis.

The applicant markets such a prosthesis under the name "Priform". This product substantially comprises a shaping support shell of plastic which is accommodated in a fabric part and has a hollow space at the rear side in which a filler material can be accommodated. The support shell cannot, however, reproduce either the touch properties or the movement properties of a natural breast.

A breast prosthesis made from a flexible plastic body to whose rear side an elastic fabric part is welded is known from EP 0 808 615 A1. Filler material which can serve the adaptation to a changing size of the remaining breast can be accommodated in a hollow space between the fabric part and the plastic body. The fabric part is, however, inseparably connected to the plastic body and cannot be removed for washing, which can be disadvantageous from hygienic aspects.

It is the object of the invention to provide an improved breast prosthesis which can be adapted to a changing scar structure or to a changing size of the remaining breast.

This object is achieved by a breast prosthesis in accordance with claim 1. Advantageous embodiments result from the dependent claims.

A breast prosthesis is thus provided in accordance with the invention having a support shell which is accommodated in a fabric cover. At least one filling chamber to receive a filler material is located at the rear side of the breast prosthesis. The breast prosthesis has a silicone shell which is arranged in front of the support shell and which is removably accommodated in the fabric cover.

The breast prosthesis in accordance with the invention can comprise the named components or can consist thereof. The silicone shell and/or the support shell is/are preferably completely surrounded by the fabric cover. The side of the breast prosthesis remote from the carrier is called the front side of the breast prosthesis in accordance with the invention. The side facing the carrier is called the rear side.

The breast prosthesis can be continuously adapted during an initially described course of reconstruction which is accompanied by a successfully changing size of the remaining breast thanks to the accommodation of variable quantities of a filler material in the at least one filling chamber. The volume of the breast prosthesis is in this respect preferably regulated so that the total volume of the operated side (remaining breast+prosthesis) is always adapted to the healthy breast. Furthermore, the breast prosthesis in accordance with the invention acts as a protection for the pain-sensitive freshly operated tissue due to the presence of a support shell. The silicone shell can be simply removed from the fabric cover to wash it. The breast prosthesis in accordance with the invention is thus advantageous from hygienic aspects.

A soft and natural outward appearance is achieved by the forward arrangement of the silicone shell in front of the support shell. The natural outward appearance and the natural touch properties also allow, in addition to the use as a prosthesis for first care, a furthergoing use as a multifunctional light prosthesis. The weight can be reduced by approximately 50% with respect to standard prostheses by the combination of a flat silicone shell with a support shell, which provides an additional weight saving even over commercial light prostheses.

A breast prosthesis in accordance with the invention is thus mainly used during the expander treatment as preparation for an implant or as a light prosthesis.

The support shell is preferably areal and of shell shape and has a convexly shaped front side. It can have a depth or thickness which is constant over its area, with it optionally being able to taper in the marginal regions.

The silicone shell is preferably likewise areal and of shell shape and has a convexly shaped front side which is based on the natural shape of the female breast. The rear side is preferably of concave design and can form the counterpiece to the convex front side of the support shell. The depth or thickness of the silicone shell is preferably larger in the central region than in the marginal regions. The silicone shell can be very thin in the marginal regions and can optionally only have the thickness of a plastic film which can form the envelope of the silicone shell. The silicone shell is typically thicker than the support shell at least in its central region, with the thickness of the silicone shell also being able to be at least twice or also at least three times the thickness of the support shell. The thickness of the silicone shell is, however, advantageously also restricted to a specific maximum value and amounts, for example, to less than ten times, and further preferably less than five times, the thickness of the support shell.

In an embodiment, the support shell is fixedly connected to the fabric cover. This connection can take place, for example, in a ring-shaped and areal marginal region at the rear side of the support shell. The marginal region typically surrounds a central area at the rear side of the support shell and extends over a specific thickness up to the margin of the support shell. Suitable kinds of connection of the fabric cover to the support shell include inter alia welding, adhesive bonding and sewing.

Alternatively, the support shell can be removed from the fabric cover. In this connection, for example, a semi-fixed connection of the support shell to the fabric cover is conceivable, for example via a hook and loop fastening.

In an embodiment, the filling chamber is arranged at the rear side of the support shell in the central region.

In an embodiment, the support shell and the silicone shell are directly adjacent to one another within the fabric cover so that no element of the fabric cover is located between the support shell and the silicone shell. Alternatively, the support shell and the silicone shell can, however, also be accommodated in different reception chambers of the fabric cover.

In an embodiment, the silicone shell is disposed in front of the support shell over the full area. In this respect, the rear-side surface of the silicone shell should substantially correspond to the front-side surface of the support shell.

In an embodiment, the fabric cover has at least two areal fabric parts which are connected along their common margin. The fabric cover can also comprise these fabric parts. These fabric parts can, for example, be sewn, welded or adhesively bonded in the region of their common margin.

In an embodiment, the fabric cover has an opening for the removal of the silicone shell. The opening can, for example, be an opening slit which is applied to the lower side of the prosthesis. This opening or this opening slit can be closable or non-closable. Possible closure mechanisms are, for example, hook and loop closures, zipper fasteners, hooks and eyelets, press fasteners or overlapping and optionally tensioned sections of the fabric cover. The opening can be located, if present, in the connection region of a plurality of fabric parts forming the fabric cover or extend at their connection line.

In the case of a removable arrangement of the support shell, the same opening can also serve the removal of the support shell. Alternatively, with such an arrangement, a further opening can be provided which in an embodiment can likewise have one or more of the properties described in connection with the opening for the removal of the silicone shell.

In an embodiment, the fabric cover comprises a preferably elastic synthetic fiber fabric. Alternatively to this, a natural fiber such as cotton can also be used. The production from microfiber fabric is preferred which can in particular include microfibers of polyester and/or polyamide. Such breathable fabrics support the removal of moisture from the skin.

In an embodiment, the front side and/or the rear side of the fabric cover of the breast prosthesis in accordance with the invention is/are tensioned. This in particular applies if the silicone shell is accommodated in the fabric cover next to the support shell. This tension can be achieved on the production side by the deep drawing, for example molding, of an elastic fabric cover as part of the shaping of the support shell and/or of the silicone shell.

In an embodiment, the filling chamber is at least partly bounded by the fabric cover and/or the rear side of the support shell. The filling chamber can, for example, be formed as an intermediate space between the rear side of the support shell and the fabric cover or can be defined by the rear side of the support shell and the fabric cover. The filling chamber therefore preferably directly contacts the rear side of the support shell, as a rule in its central region. The filling chamber can, for example, extend over that region of the rear side of the support shell in which the support shell, if applicable, is not fixedly connected to the fabric cover. In the region of the chamber, the fabric cover can be made as tensioned or also as loose.

In an embodiment, the filling chamber has an opening for the removal of the filler material. It can, for example, be located inside the fabric cover at the rear side of the filling chamber or in the connection region of the fabric cover and the support shell. The opening is preferably an opening slit which can be closable or also non-closable. Suitable closure mechanisms, for example, include overlapping and optionally tensioned sections of the fabric cover in the marginal regions of the opening or hook and loop closures.

In an embodiment, a filler material is received in the filling chamber. Suitable filling materials include wad-shaped materials such as fiber wads or thread wads, which are understood in the present invention as a loose volume structure of fibers or threads. Alternatively or additionally to the wad-shaped filling material, one or more cushion bodies can be accommodated in the filling chamber, which is understood as a fabric shell or film which in turn surrounds a filling material.

Wadding is in turn suitable as a filling material. Suitable materials for providing the threads or fibers for the wadding or for a fabric sleeve include cotton fibers or synthetic fibers, in particular microfibers such as polyester or polyamide. Likewise suitable filler materials are foamed plastics such as foam flakes or polystyrene as well a hollow spheres or gels.

In an embodiment, the breast prosthesis has a plurality of filling chambers, for example two or three individual chambers. In some cases (partial operations, unsuccessful reconstructions, etc.), a better shape adaptation to the remaining breast disposed under the prosthesis can thus be achieved. Provision can in this respect be made that in an application-specific manner only a plurality or also all individual filling chambers are filled. In an embodiment, the individual filling chambers can be arranged laterally next to one another. Arrangements are also conceivable and covered by the invention as strips or layers lying over one another, as concentric circles, in a chessboard pattern or individually adapted. Optionally, the individual chambers can be separated from one another by seams or weld seams. Each chamber can thus be formed as an intermediate space between the rear side of the support shell and the fabric cover. Each individual chamber can have an opening for the removal of the filler material such as was described in more detail in connection with a single chamber.

In an embodiment, the support shell is made of plastic. In this respect, it is preferably a soft or elastic plastic which should, however, be of stable form, i.e. not plastically deformable. The use of soft polyurethane foams or of spacer fabrics such as are typically also used in the shells of a brassiere is preferred, for example.

In an embodiment, the silicone shell is a soft elastic plastic body which preferably comprises a silicone mass welded into a plastic film. The plastic film can be a PU film. Examples for suitable silicone masses include inter alia a two-component silicone rubber mass.

Further details and advantages of the invention result from the following embodiments described with reference to the FIGURE.

The only FIGURE shows a representation of a breast prosthesis in accordance with the invention in cross-section.

The breast prosthesis is generally marked by the reference numeral 1. It has a support shell 2 made from a soft PU foam which has a constant thickness and is of shell shape. This shell has a somewhat smaller thickness in the end regions.

A soft elastic silicone shell 3 which is composed of a two-component silicone rubber mass welded into a PU film adjoins the front side of the support shell 2 over the full area. The silicone shell 3 has a design at its outer side which is based on the natural shape of the breast. The concave inner side is adapted to the curvature of the outer side of the support shell 2. The thickness of the silicone shell is larger in the central region than in the marginal regions where it converges acutely.

The support shell 2 and the silicone shell 3 are accommodated in a fabric cover 4 which comprises areal fabric parts 4a and 4b which are connected along their common margin.

The support shell 2 is sewn to the fabric cover 4 along the inner edge 2c of a ring-shaped marginal region 2a at its rear side.

In the central region 2b at the rear side of the support shell, a filling chamber 5 is located which is filled with wadding. This wadding can be introduced and removed through the opening slit 7 in the fabric cover. The chamber 5 is defined by the rear side of the support shell 2 and by the fabric cover 4.

An opening 6 through which the silicone shell 3 can be removed as required is located in the connection region of the fabric parts 4a and 4b at the lower side of the breast prosthesis. Not only a hygienic advantage in the washing of the breast prosthesis thereby results, but also the possibility of equipping it with differently shaped silicone shells 3.

In summary, it results that a breast prosthesis in accordance with the invention can be adapted in a simple manner to a changing scar structure or size of the remaining breast, has a low weight and can simultaneously satisfy increased esthetic demands.

The invention claimed is:

1. A breast prosthesis having a front side and a rear side, the breast prosthesis comprising:
   a fabric cover;
   a support shell having a front side and a rear side, the support shell comprising soft polyurethane foam, the support shell being accommodated in the fabric cover, at least a portion of the rear side of the support shell being fixedly connected to the fabric cover;
   one or more filling chambers for accommodating a filler material, the one or more filling chambers being located behind the support shell at the rear side of the breast prosthesis and
   a silicone shell arranged in front of the front side of the support shell, the silicone shell being directly adjacent the soft polyurethane foam of the support shell, the silicone shell being accommodated in a removable manner in the fabric cover, the fabric cover having an opening for removal of the silicone shell;
   wherein the support shell, the one or more filling chambers, and the silicone shell are completely surrounded by the fabric cover.

2. A breast prosthesis in accordance with claim 1, wherein the one or more filling chambers contains filling material, and the silicone shell and the fabric cover cushioned with filler material can be worn and washed separately.

3. A breast prosthesis in accordance with claim 1, wherein the support shell is fixedly connected to the fabric cover in a ring-shaped and areal marginal region at the rear side of the support shell.

4. A breast prosthesis in accordance with claim 1, wherein the one or more filling chambers are arranged in a central region at the rear side of the support shell.

5. A breast prosthesis in accordance with claim 1, wherein the silicone shell covers the support shell.

6. A breast prosthesis in accordance with claim 1, wherein the fabric cover comprises at least two areal fabric parts which are connected along their common margin.

7. A breast prosthesis in accordance with claim 1, wherein the opening of the fabric cover is closable for removal of the silicone shell.

8. A breast prosthesis in accordance with claim 7, wherein the opening of the fabric cover for removal of the silicone shell is provided with a hook and loop closure, a zipper fastener, hooks or eyelets, press fasteners or overlapping sections of the fabric cover.

9. A breast prosthesis in accordance with claim 8, wherein the overlapping sections of the fabric cover are tensioned.

10. A breast prosthesis in accordance with claim 1, wherein the one or more filling chambers are at least partly bounded by the fabric cover.

11. A breast prosthesis in accordance with claim 1, wherein the one or more filling chambers are formed as an intermediate space between the rear side of the support shell and the fabric cover.

12. A breast prosthesis in accordance with claim 1, wherein the one or more filling chambers contains filling material, and the one or more filling chambers have an opening for removal of the filler material.

13. A breast prosthesis in accordance with claim 1, further comprising a filler material in the one or more filling chambers.

14. A breast prosthesis in accordance claim 13, wherein the filler material is a material selected from the group consisting of wadding, foamed plastics, foam flakes, polystyrene, hollow spheres and gels.

15. A breast prosthesis in accordance with claim 1, wherein the support shell comprises shape-stable plastic.

16. A breast prosthesis in accordance with claim 15, wherein the shape stable plastic is elastic.

17. A breast prosthesis in accordance with claim 15, wherein the shape stable plastic is soft.

18. A breast prosthesis in accordance with claim 1, wherein the silicone shell is a soft elastic plastic body.

19. A breast prosthesis in accordance with claim 18, wherein the silicone shell comprises a silicone mass welded in a plastic film.

20. A breast prosthesis in accordance with claim 1, wherein the one or more filling chambers are at least partly bounded by the rear side of the support shell.

21. A breast prosthesis in accordance with claim 1, wherein the support shell is fixedly connected to the fabric cover by a welding, adhesive bonding or sewing.

* * * * *